(12) United States Patent  
New et al.

(10) Patent No.: US 9,471,637 B2
(45) Date of Patent: Oct. 18, 2016

(54) DATA SELECTION

(75) Inventors: John Philip New, Salford (GB); John Martin Gibson, Salford (GB); Iain Edward Buchan, Manchester (GB); John David Ainsworth, Manchester (GB)

(73) Assignees: THE UNIVERSITY OF MANCHESTER (GB); SALFORD ROYAL NHS FOUNDATION TRUST (GB)

( * ) Notice: Subject to any disclaimer, the term of this patent is extended or adjusted under 35 U.S.C. 154(b) by 0 days.

(21) Appl. No.: 13/380,423

(22) PCT Filed: Jun. 8, 2010

(86) PCT No.: PCT/GB2010/001119
§ 371 (c)(1),
(2), (4) Date: Apr. 11, 2012

(87) PCT Pub. No.: WO2010/149948
PCT Pub. Date: Dec. 29, 2010

(65) Prior Publication Data
US 2012/0191749 A1   Jul. 26, 2012

(30) Foreign Application Priority Data

Jun. 23, 2009   (GB) .................................. 0910874.7

(51) Int. Cl.
*G06F 17/30*   (2006.01)
*G06F 19/00*   (2011.01)
(Continued)

(52) U.S. Cl.
CPC ... *G06F 17/30477* (2013.01); *G06F 17/30522* (2013.01); *G06F 19/322* (2013.01); *G06F 19/363* (2013.01); *G06F 21/6254* (2013.01)

(58) Field of Classification Search
CPC ........................ G06F 19/322; G06F 21/6254
USPC .............................................. 707/769; 705/3
See application file for complete search history.

(56) References Cited

U.S. PATENT DOCUMENTS

2003/0065669 A1\* 4/2003 Kahn et al. ................... 707/100
2004/0078238 A1   4/2004 Thomas et al.
(Continued)

FOREIGN PATENT DOCUMENTS

WO   WO0122323       3/2001
WO   WO02084531      10/2002
WO   2005098736 A2   10/2005

OTHER PUBLICATIONS

United Kingdom Intellectual Property Office Search Report for GB Application No. GB0910874.7, dated Sep. 24, 2009 (1 page).
(Continued)

*Primary Examiner* — Alex Gofman
(74) *Attorney, Agent, or Firm* — One3 IP Management, P.C.; Justin G. Sanders; Peter D. Weinstein (57) ABSTRACT

A method of selecting data, the method comprising, receiving data indicating a first requirement and identifying first records stored in a first database. The first records relate to first data subjects and the identification is based upon the first requirement. The first data subjects cannot be identified from the records of the first database. Second records are identified, the second records being stored in a second database and relating to the first data subjects. The first data subjects can be identified from the identified records of the second database. Each of the second records corresponds to a respective one of the first records, and the identification of the second records is based upon the first requirement.

20 Claims, 7 Drawing Sheets

(51) Int. Cl.
    *G06F 21/62*   (2013.01)
    *G06F 15/16*   (2006.01)

(56) References Cited

U.S. PATENT DOCUMENTS

| | | | |
|---|---|---|---|
| 2005/0188421 A1* | 8/2005 | Arbajian | 726/4 |
| 2008/0010254 A1* | 1/2008 | Settimi | 707/3 |
| 2008/0091474 A1 | 4/2008 | Ober et al. | |
| 2009/0112629 A1 | 4/2009 | Leiper | |
| 2010/0114920 A1* | 5/2010 | Srivastava et al. | 707/757 |

OTHER PUBLICATIONS

PCT International Search Report, Jul. 3, 2011.
Pommering, Klaus, et al., "Secondary Use of the EHR via Pseudonymisation," Studies in Health Technology and Informatics, Jan. 1, 2004, pp. 1-24, vol. 103, I O S Press, Amsterdam, NL.

* cited by examiner

| 30 Patients | |
|---|---|
| 31 — PatientID | |
| Title | |
| Surname | |
| Forenames | |
| MaritalStatus | |
| Sex | — 34a |
| DOB | — 34b |
| Address1 | |
| Address2 | |
| Address3 | |
| Address4 | |
| Address5 | |
| 34 { PostCode | — 34c |
| HomeTelephone | |
| WorkTelephone | |
| MobileTelephone | |
| Deceased | — 34d |
| DeathDate | — 34e |
| Height | — 34f |
| Weight | — 34g |
| Religion | |
| EthnicOrigin | — 34h |
| Email | |
| Occupation | |
| GPCode | |
| GPPracticeCode | |
| GPPracticeName | |
| GPName | |
| GPTitle | |
| GPInitials | |
| GPSurname | |
| GPAddress1 | |
| 35 { GPAddress2 | |
| GPAddress3 | |
| GPAddress4 | |
| GPAddress5 | |
| GPPostCode | |
| GPTelephone1 | |
| GPTelephone2 | |
| GPDoH | |
| GPID | |
| UpdatedDate | — 36 |

| 40 Journal | |
|---|---|
| PatientID | — 41 |
| EntryDate | — 44 |
| Rubric | — 45 |
| ReadCode | — 46 |
| CodeValue | — 47 |
| CodeUnits | — 48 |
| UpdatedDateTime | — 49 |
| Source | — 50 |

DATA SELECTION

RELATED APPLICATION

This application claims priority to PCT application PCT/GB2010/001119 filed Jun. 8, 2010, which claims priority to British patent application GB 0910874.7 filed Jun. 23, 2009.

The present invention relates to a method of selecting data. The present invention has particular, but not exclusive, application in allowing the selection of data to which a user has limited access.

Computers are now widely used in a variety of different applications. One particular application relates to the storage of data relating to individuals (sometimes referred to as data subjects) so as to allow that data to be readily available and easily processed. In some cases data relating to large numbers of individuals is stored in a centralized database.

While the storage of data relating to individuals provides benefits both for organizations using that data, the individuals themselves and society at large, there are dangers inherent in centralized storage of large quantities of personal data. For example, many individuals are concerned that their personal data will become known to unauthorized persons who may use the data for illegitimate purposes.

Given the widespread benefits of centralized storage in a variety of fields of activity, considerable effort has been put into securing data so as to ensure that data can only be accessed by authorized users in a controlled manner.

While controlling access to data is important, many currently employed schemes lack flexibility and control access in such a way that users who are not authorized are provided with no access to the stored data. Such an arrangement can cause inefficiencies in that some users who are not authorized to access all of the data, have legitimate cause to access parts of the data, and restrictions preventing all access therefore deprive such users of the benefits of centralized data storage.

Clinical trials may be conducted for a number of purposes, for example to further research into particular treatments for diseases. In many countries, medical researchers are required to conduct clinical trials in order to ascertain and document the safety and efficacy of new medical treatments or devices before those new medical treatments or devices can be authorized for use within that country. Before a clinical trial can begin, a number of steps are often necessary, including a feasibility assessment to determine whether there are enough potential participants to conduct the clinical trial, and subsequently, recruitment of participants.

Individuals determining clinical trial feasibility often do not have access to centralized medical records databases because they are not authorized to access the sensitive personal information contained within such databases. As such, clinical trial feasibility is often assessed on an unstructured basis, by asking clinical staff, such as doctors, for estimates of how many patients with particular characteristics they might expect to see in a given time period. Based on the clinicians' responses, a researcher can estimate, for each clinician willing to involve their patients in a clinical trial, how many eligible patients that clinician is likely to see over the course of the trial. With short deadlines inaccurate estimation of the number of potential eligible participants is common.

Clinical teams may be involved with a number of concurrent clinical trials, each with a different procedure for seeking informed consent during recruitment. The process of recruitment is therefore often laborious and unstructured.

There is therefore a need for more efficient clinical trial feasibility assessment and recruitment processes.

It is an object an embodiment of the present invention to obviate or mitigate one or more of the problems outlined above.

According to a first aspect of the present invention, there is provided a method of selecting data. The method comprises receiving data indicating a first requirement; identifying first records stored in a first database, the first records relating to first data subjects and the identification being based upon said first requirement, wherein said first data subjects cannot be identified from the records of the first database; and identifying second records stored in a second database, the second records relating to said first data subjects, wherein said first data subjects can be identified from the identified records of the second database and each of said second records corresponds to a respective one of said first records, and said identification of said second records is based upon said first requirement.

Given that data subjects cannot be identified from records of the first database, data stored within the first database is of relatively low sensitivity, as compared to the data stored in the second database from which the data subjects can be identified. As such, the present inventors have realized that it can be useful to identify records of interest in the first database, and only when records of interest have been identified (based upon the first requirement) to identify records in the second database. Users may have more limited access to the second database, but even if this is the case, the first database can be used to identify records of interest without jeopardizing the security of personal information. For example, by querying the first database a user may be able to determine whether a sufficient number of records satisfy a certain criterion, and if this is the case, the user can then seek to obtain data based upon the identified records stored in the second database. The user may have limited, or no access to the second database, and as such, having queried the first database, the user may request that a third party, authorized to access the records in the second database, perform a desired action based upon the identified records. For example, the user may request that a third party corresponds with individuals to whom the identified record relate.

Identification of the second records may be based upon a second requirement. The second requirement may be based upon a modification of said first requirement, or may alternatively be identical to the first requirement.

The first requirement may take the form of a first a database query and the second records may be identified based upon a second database query. The first database query may be processed to generate said second database query.

The method may further comprise receiving a selection of some of said second records and processing said selected second records. For each respective second record, a first user associated with the respective second record may be identified. The identified first user may be, for example, a user having authorized access to the respective second record. Each respective second record may be provided to the respective identified first user. The or each respective first user may only be provided with second records relating to data subjects associated with the respective first user. As such, access to particular ones of the second records may be restricted to appropriate authorized users.

Said selection of some of said second records may be received from at least one of said first users. Said data indicating a first requirement may be received from a second user. The second user may be provided with access to said selected second records.

Processing said selected second records may be based upon receiving data from the first data subjects associated with said selected second records. For example, the processing may be based upon consent received from the relevant first data subjects. The data received from the first data subjects may therefore comprise data indicating authorisation for a second user to be provided with access to said selected second records.

Receiving a selection of some of said second records may comprise receiving from at least one of said first users a selection of at least some second records provided to the respective first user.

The method may further comprise providing an indication of a number of data subjects based upon the received selection of second records.

Providing a second record to a first user may further comprise providing an indication of said first requirement to the first user.

The method may further comprise providing a first indication of a number of data subjects based upon said identified first records. It may be determined whether said first indication is acceptable. The second records may be identified if but only if it is determined that said first indication is acceptable. The first indication may be provided to said second user, and determining whether said first indication is acceptable may be based upon input received from said second user. If it is determined that said first indication is unacceptable, the method may comprise identifying further first records stored in the first database, the identification being based upon a third requirement.

The method may further comprise processing records in said second database to generate records for insertion into said first database. The processing may comprise selecting at least one record from said second database; identifying first data in said at least one record from which data subjects can be identified; processing said first data to generate second data from which data subjects cannot be identified; storing said second data in said first database.

The first users may be clinicians. The second users may be researchers, and said researches may not be authorised to access records from which data subjects can be identified (i.e. records of the second database). The data subjects may be patients, such that the data stored in the first and second databases is clinical data. Aspects of the invention have application in determining the feasibility of a clinical trial. More specifically, a researcher may make use of the first database to determine how many patients (identified by records of the first database) meet a particular requirement. The researcher may then request that a clinician reviews records of the second database corresponding to the records of interest in the first database, so as to determine whether sufficient patients exist for the clinical trial to be feasible.

Once it has been demonstrated that a particular clinical trial is feasible, eligible participants can be identified and approached in order to obtain informed consent from that participant to enroll that participant in the clinical trial. This process, which requires access to records of the second database can be carried out by a clinician having authorized access to the second database. A potential participant may be approached by that patient's attending clinician during a clinical encounter, or by notification such as a letter.

The methods described herein allow clinical trial feasibility to be assessed while respecting the requirement of 'Consent for Consent' that defines the consent required to search an individual's health record to determine whether or not they should be invited to participate in a clinical study. That is, Consent for Consent may be considered to be the consent required to obtain consent from a participant.

It will be appreciated that aspects of the invention can be implemented in any convenient form. For example, the invention may be implemented by appropriate computer programs which may be carried out appropriate carrier media which may be tangible carrier media (e.g. disks) or intangible carrier media (e.g. communications signals). Aspects of the invention may also be implemented using suitable apparatus which may take the form of programmable computers running computer programs arranged to implement the invention.

Embodiments of the present invention are now described, by way of example, with reference to the accompanying drawings in which.

Figure 1:
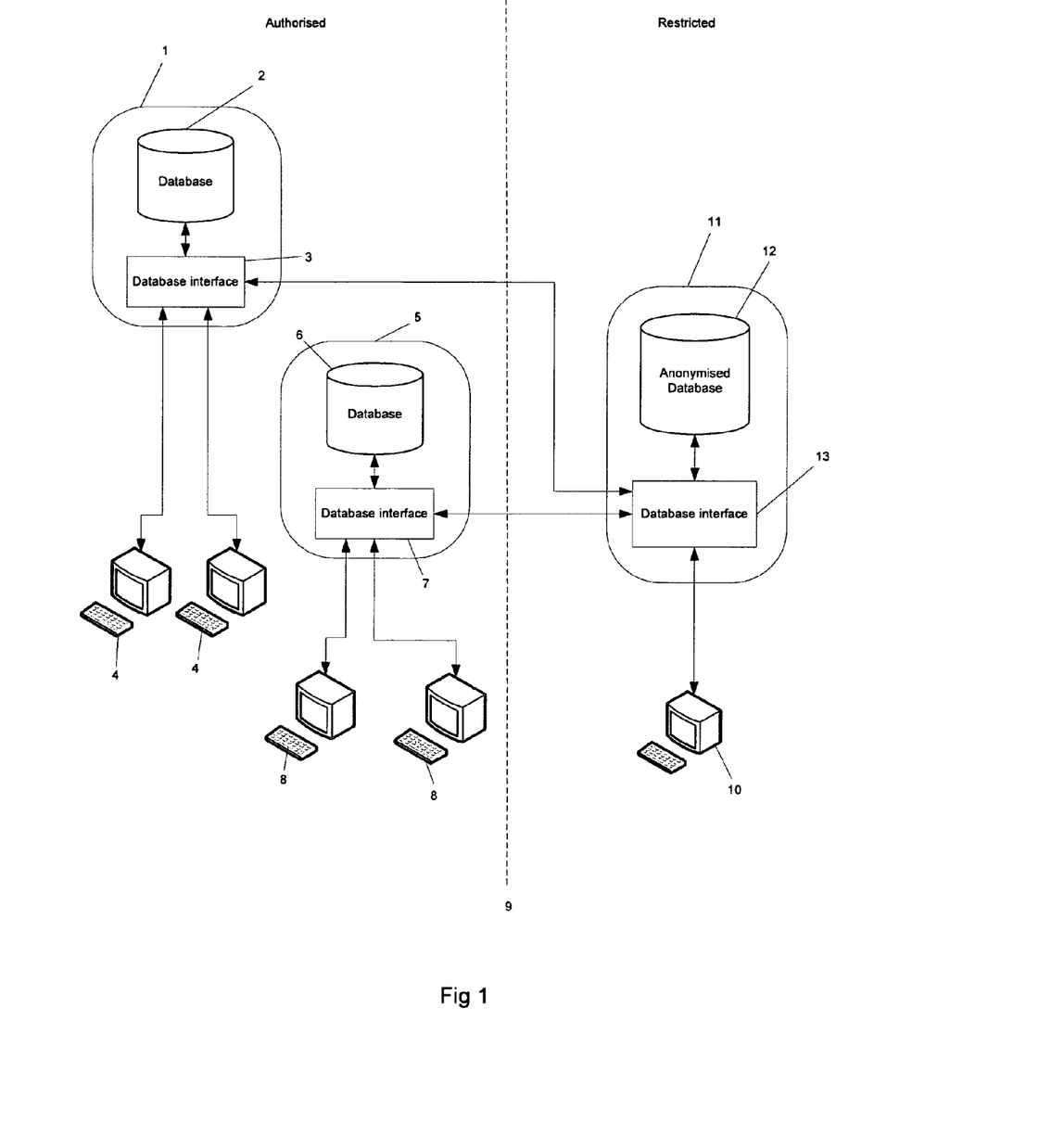
FIG. 1 is a schematic illustration of a system in which a client is provided with controlled access to data in an anonymous form in accordance with an embodiment of the present invention.

Referring to FIG. 1, there is shown a general overview of a system in accordance with an embodiment of the present invention. A server 1 hosts a database 2 storing subject-identifiable data. That is, the database 2 stores records relating to individual data subjects from which those data subjects can be identified. The server 1 provides an interface 3 to the database 2 through which one or more authorized users of client computers 4 access records of the database 2. Similarly, a server 5 hosts a database 6 storing subject-identifiable data and provides access to the database 6 through a database interface 7. Authorized users can use client computers 8 to access the records in the database 6 through the database interface 7. Authorization to access the subject-identifiable data stored in either one of the databases 2, 6 is strictly controlled such that personal data associated with the data subjects identifiable from the databases 2, 6 can be accessed only by authorized users using the client computers 4, 8 respectively.

Figure 1A:
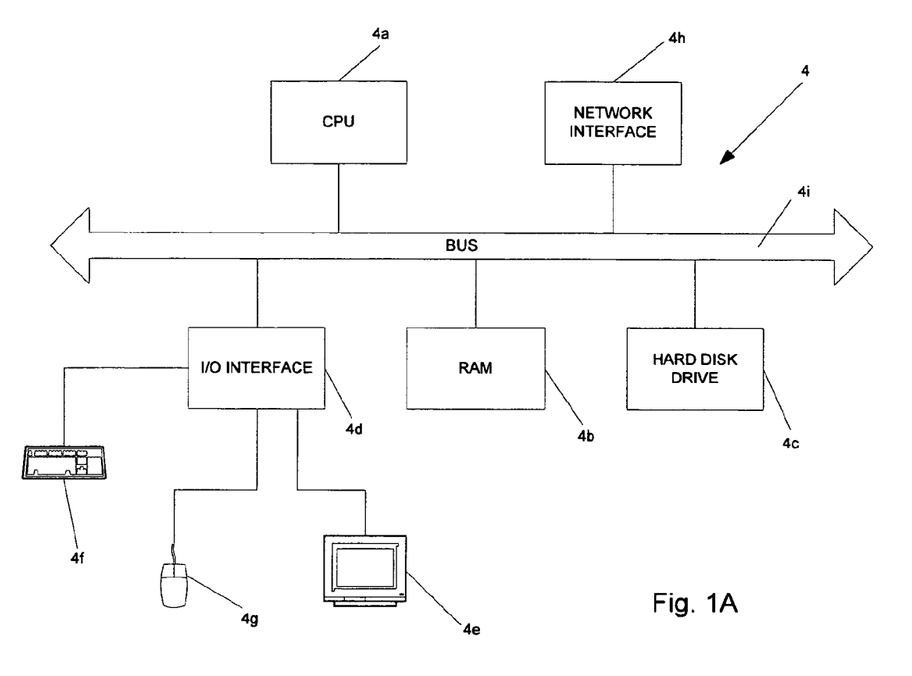
FIG. 1A is a schematic illustration of the client of FIG. 1.

FIG. 1A shows the client computer 4 in further detail. It will be appreciated that the client computers 8 and the servers 1, 5 may take a similar general form. It can be seen that the client computer 4 comprises a CPU 4a which is configured to read and execute instructions stored in a volatile memory 4b which takes the form of a random access memory. The volatile memory 4b stores instructions for execution by the CPU 4a and data used by those instructions.

The client computer 4 further comprises non-volatile storage in the form of a hard disc drive 4c. The client computer 4 further comprises an I/O interface 4d to which are connected peripheral devices used in connection with the computer 4. More particularly, a display 4e is configured so as to display output from the computer 4. Input devices are also connected to the I/O interface 4d. Such input devices include a keyboard 4f and a mouse 4g which allow user interaction with the computer 4. A network interface 4h allows the computer 4 to be connected to an appropriate computer network so as to receive and transmit data from and to other computing devices, such as the server 1. The CPU 4a, volatile memory 4b, hard disc drive 4c, I/O interface 4d, and network interface 4h, are connected together by a bus 4i.

Further users are not authorized to access the subject-identifiable data stored in either of the databases 2, 6. While, generally speaking, the further users are not authorized to access the subject-identifiable data, it is desirable allow the further users to access particular data in the databases 2, 6 where that data meets certain criteria. It is further desirable that the further users can search for the presence of data meeting those criteria, while maintaining the privacy of the data subjects to which the records of the databases 2, 6 relate. More specifically, the further users should be allowed to access and query data stored in the databases 2, 6 to the extent that it is possible to do so without identifying the data subjects to whom the data relates.

To provide access to the data of the databases 2, 6 while maintaining the requirement of privacy, a server 11 is configured to host an anonymised database 12 and to make the database 12 accessible to the further users via a client computer 10 which can access the database 12 through a database interface 13. The anonymised database 12 contains anonymised versions of at least some of the records in the databases 2, 6. In this way, a user of the client computer 10 can query the anonymised database 12 through the database interface 13 to determine the presence of data meeting particular criteria, without being able to identify individuals to whom that data relates. The server 11 and client computer 10 can take a similar form to that illustrated in FIG. 1A.

If it is determined that data in the anonymised database 12 meets some criteria specified by a user of the client computer 10, the user can request that further action is taken, by, for example an authorized user of one of the client computers 4, 8, where the further action requires access to the subject-identifiable data stored in the databases 2, 6. Alternatively, the user of the client computer 10 may request authorization to access the corresponding data from one of the databases 2, 6. In this way, a user of the client computer 10 can determine the existence of data meeting specific criteria, without having access to subject-identifiable data to which the user of the client computer 10 is not authorized, and then request that an authorized user of one of client computers 4, 8 perform a desired action based upon the identified records. For example, the user of the client computer 10 may wish to correspond with data-subjects to whom the identified records relate, and can request that a user of the client computers 4, 8 (authorized to access the subject-identifiable records of the databases 2, 6) initiate correspondence on behalf of the user of the client computer 10.

In general terms, a line 9 provides a separation between users of the client computers 4, 8 who are authorized to access data from which individuals can be identified stored in one of the databases 2, 6, and users of the client computer 10 who are not so authorized.

An embodiment of the present invention is now described in more detail using an example of clinical trial feasibility determination and clinical trial recruitment.

Figure 2:
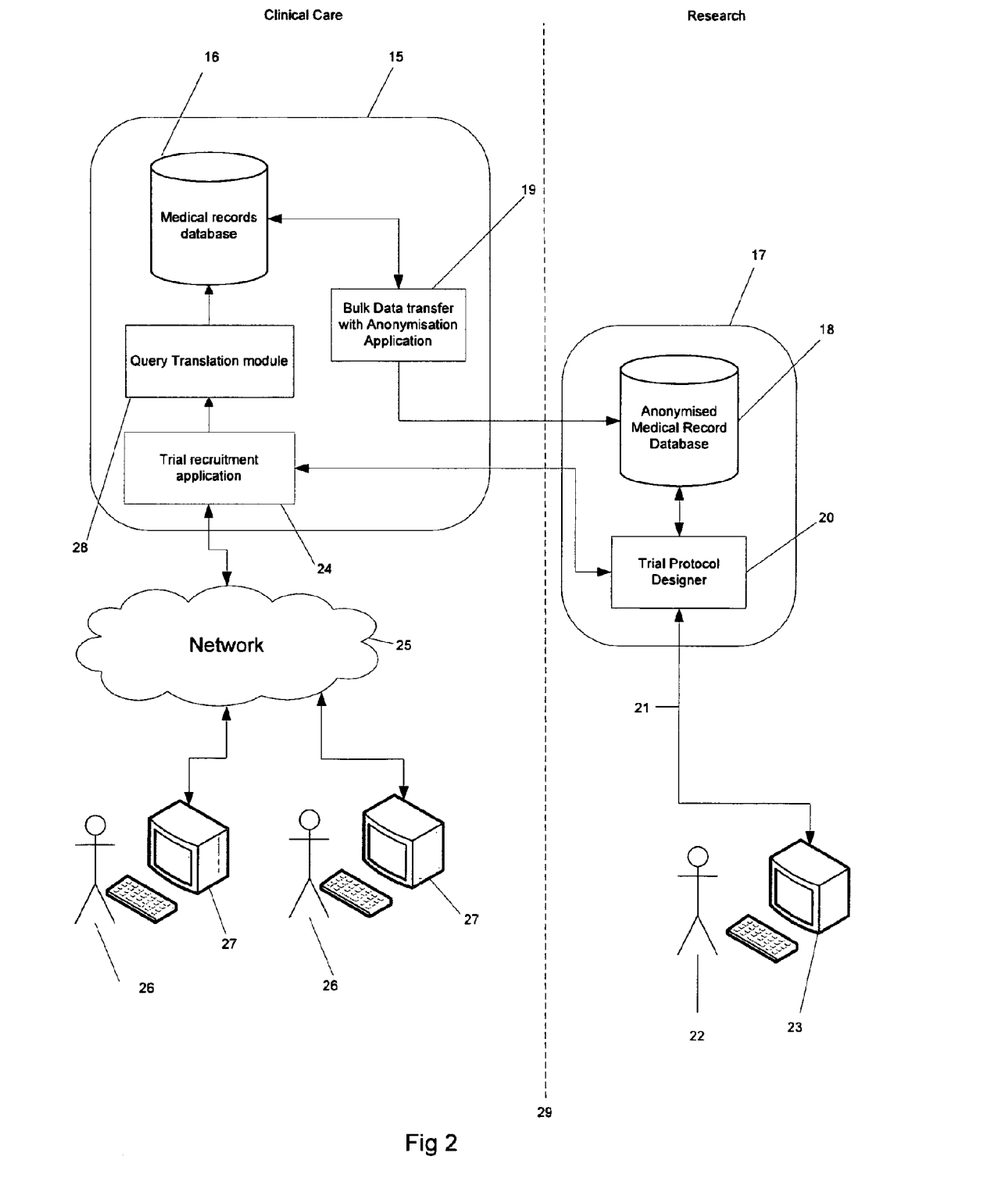
FIG. 2 is a schematic illustration of an architecture of a system for implementing an embodiment of the present invention.

FIG. 2 is a schematic illustration of a system arranged in accordance with an embodiment of the present invention. A server 15 is configured to host a medical records database 16 containing a plurality of patient-identifiable medical records. That is, a medical record in the medical records database 16 contains data that can be used to identify the patient to whom that medical record relates. The medical records database 16 may be a live medical records database used by clinicians to store and access data or a mirror of a live medical records database.

A second server 17 is configured to host an anonymised medical records database 18 containing anonymised versions of at least some of the medical records stored in the medical records database 16. The anonymised medical records database 18 is populated from the medical records database 16 using a data transfer and anonymisation application 19 running on the server 15. The data transfer and anonymisation application 19 is adapted to obtain data from the medical records database 16, anonymise that data, and insert the anonymised data into the anonymised medical records database 18. Details of the operation of the data transfer and anonymisation application 19 are described below with reference to FIGS. 4 and 5.

The server 17 is further configured to run a trial protocol design application 20, accessible over a network connection 21 by a clinical trial designer 22 using a client computer 23. While the client computer 23 is shown in FIG. 2 as a PC, it will be appreciated that the client computer 23 may be any device capable of accessing the trial protocol design application 20 over the network connection 21. The network connection 21 can take any suitable form, and may be an Internet connection. The trial design application 20 may be accessed using the Secure Hypertext Transfer Protocol (HTTPS).

The trial protocol design application 20 is configured to communicate with the anonymised medical records database 18, using, for example, appropriate SQL commands. The trial protocol design application 20 is further adapted to communicate with a trial recruitment application 24 running on the server 15. The trial recruitment application 24 is accessible through a network 25 by clinicians 26 using client computers 27. The network 25 may be any suitable network, and may be the Internet. The trial recruitment application 24 is adapted to communicate with a query translation module 28 running on the server 15, which is in turn configured to communicate with the medical records database 16, using, for example, appropriate SQL commands. Operation of the trial recruitment application 24 and query translation module 28 is described in further detail below.

A line 29 illustrates a notional clinical care boundary. On a clinical care side of the clinical care boundary 29, clinicians 26, responsible for patient care, have access to patient-identifiable information stored in the medical records database 16. On a research side of the clinical care boundary 29, the trial designer 22 does not have access to patient-identifiable information, but merely has access to anonymous data stored in the anonymised medical records database 18 as is required for the design and refinement of clinical trials. Patient-identifiable data does not cross the clinical care boundary 29.

It will be appreciated that, while there is only shown a single server 15 storing patient-identifiable data in the medical records database 16, there may be a plurality of servers each storing patient-identifiable information in respective medical records databases. For example, there may be respective medical records databases in different geographical areas. Where there is more than one server on the clinical care side of the boundary 29 storing patient-identifiable data, it may be that respective clinicians 26 can only access particular respective servers, the respective servers storing patient-identifiable data relating to patients for which the respective clinicians are responsible.

Further, the anonymised medical records database 18 may store anonymised versions of records taken from each of a plurality of medical records databases, thereby allowing a user 22 to search for data taken from a plurality of medical records databases storing patient-identifiable data without providing the user 22 with access to the patient-identifiable data stored in the plurality of medical records databases.

The structure of the databases 16, 18 and the process of anonymisation performed by the data transfer and anonymisation application 19 is now described with reference to FIGS. 3 to 5.

Figure 3:
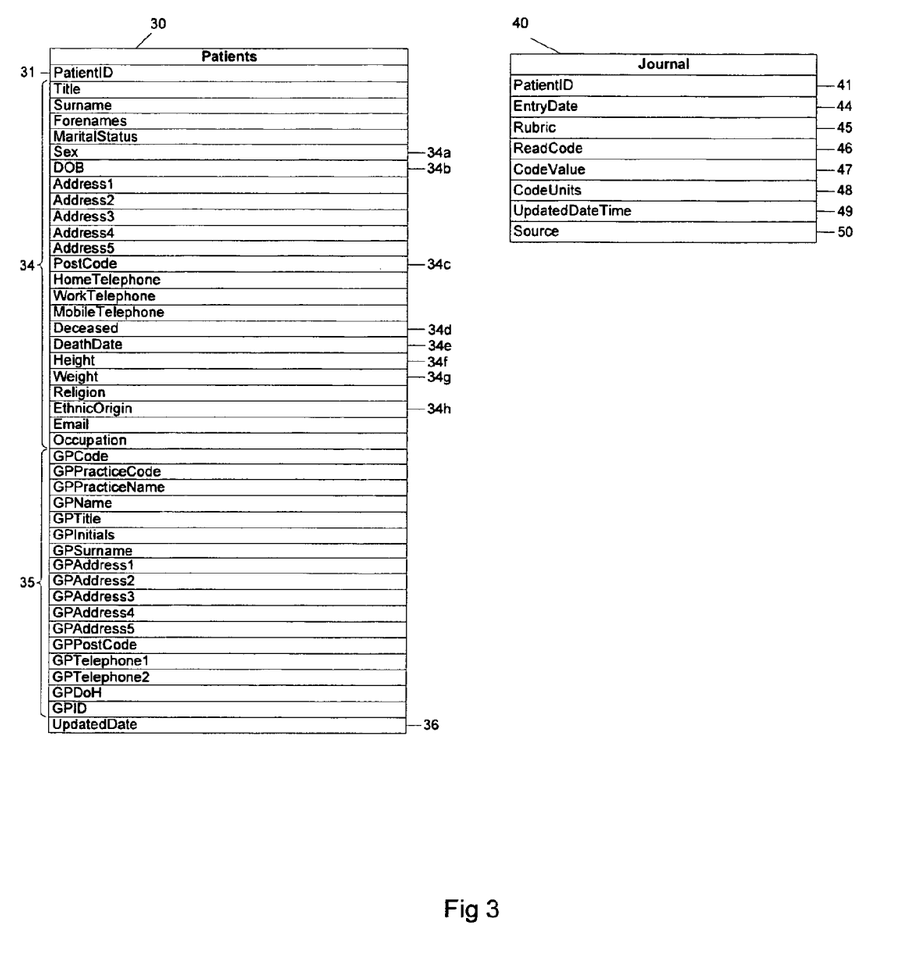
FIG. 3 is a schematic illustration of tables of a medical records database in the system of FIG. 2.

FIG. 3 schematically illustrates tables in the medical records database 16. Two tables, a Patients table 30, a Journal table 40, are shown in FIG. 3, although it will be appreciated that the medical records database 16 may contain other tables in addition to those shown in FIG. 3.

The Patients table 30 stores patient details, each patient having a single respective record in the Patients table 30. Each patient is uniquely identified by a PatientID field 31. The Patients table 30 provides a plurality of fields 34 to store a patient's personal information, including names, marital status, sex, date of birth, address, telephone numbers, whether or not that patient is deceased, date of death, height, weight, email address, religion, ethnic origin and occupation. The Patients table 30 has a further plurality of fields 35 for storing information relating to the general practitioner (GP) responsible for each patient's care. For each record, an UpdatedDate field 36 stores the date on which the record was last updated.

Each record in the Journal table 40 stores clinical information about a particular patient in the Patients table 30. For each patient in the Patients table 30, there may be a plurality of records in the Journal table 40. The patient to whom a particular record in the Journal table 40 relates is identified by a patientID field 41, which corresponds with the equivalent patientID field 31 in the Patients table 30. That is, for any record in the Journal table 40, the patient to whom that record relates can be determined by matching the patientID field 41 of that record with the patientID field 31 of that patient's record in the Patients table 30.

The date that each record is created in the Journal table 40 is recorded in an EntryDate field 44. A Rubric field 45 stores textual information which can be used to record general information regarding the clinical event which prompted the record to be entered. The textual information entered into the Rubric field 45 may, for example, be a pre-defined description of the clinical event to which the entry in the Journal table 40 relates. A ReadCode field 46 stores a code (called a Read Code) used to refer to particular clinical information in a standardised way. Read Codes cover a wide range of topics in categories such as signs and symptoms, treatments and therapies, investigations, occupations, diagnoses and drugs and appliances. A CodeValue field 47 is used to store the value of the Read Code that is being recorded and a CodeUnits field 48 stores the units in which the recorded value is measured. For example, if the subject of a particular record in the Journal table 40 is a patient's blood pressure, the ReadCode field 46 would indicate an appropriate blood pressure Read Code (for example, a Read Code "XaJ2E" may be used to record a patient's sitting systolic blood pressure) while the CodeValue field 47 would store that patient's blood pressure measurement and the CodeUnit field 48 would store the units used to measure the patient's blood pressure, for example, mmHg. If a record in the Journal table 40 is updated, the time and date of the update may be recorded in an UpdatedDateTime field 49. A Source field 50 can be used to record at which stage in a patient's care the entry in the Journal table is made, for example, the Source field 50 can be used to record whether the entry is made by during a primary or a secondary care encounter.

Figure 4:
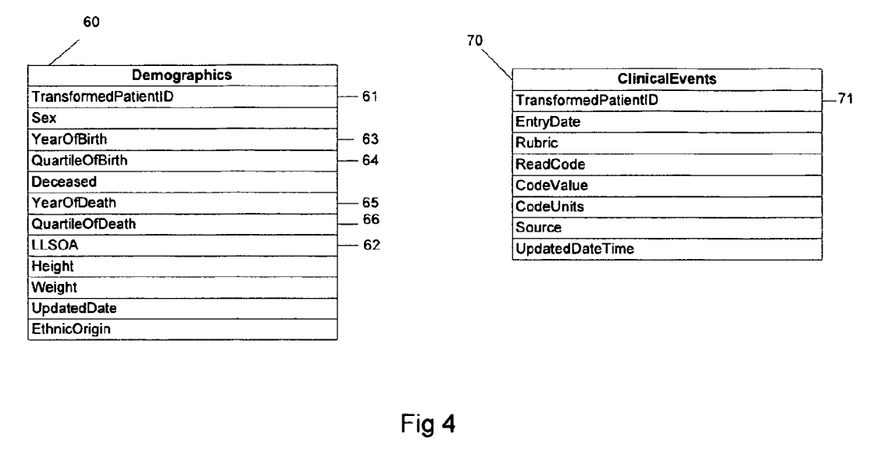
FIG. 4 is a schematic illustration of tables of an anonymous medical records database in the system of FIG. 2.

FIG. 4 schematically illustrates the tables of the anonymised medical records database 18. The anonymised medical records database 18 comprises two tables, a Demographics table 60 storing data derived from data of the Patients table 30 and a ClinicalEvents table 71 storing data derived from data of the Journal table 40.

The Demographics table 60 comprises a TransformedPatientID field 61, an LLSOA field 62, a YearOfBirth field 63, a QuartileOfBirth field 64, a YearOfDeath field 65, and a QuartileOfDeath field 66. The Demographics table 60 further comprises Sex, Deceased, Height, Weight, UpdatedDate and EthnicOrigin fields.

Figure 5:
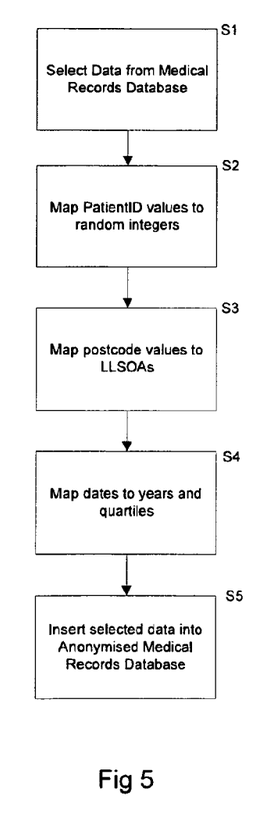
FIG. 5 is a flow chart showing processing carried out to transfer data from the medical records database into the anonymous medical records database in the system of FIG. 2.

It is now described, with reference to FIGS. 4 and 5 how the anonymisation application 19 anonymises patient-identifiable records from the medical records database 16 for insertion into the anonymised medical records database 18.

Referring to the flow chart of FIG. 5, at step S1, the data transfer and anonymisation application 19 selects a subset of records from the Patients table 30 and the Journal table 40 in the medical records database 16. The subset of records may be selected from the Journal table 40 based upon a particular condition (identified from the value of the ReadCode field 46) recorded in those records. For example, all records relating to patients having Type Two diabetes may be selected. Similarly, records from journal table 40 may be selected based on some criteria, for example, all records could be selected having an entry in the ReadCode field 46 of "Hb1Ac" and an entry in the CodeValue field 47 between 7.5% and 9.0%. Records from the Patients table 30, corresponding to the records selected from the Journal table 40 (identified based upon the PatientID fields 31, 41) can then be selected. Selection of corresponding records from the Patients table 30 may involve determining whether a particular record has already been inserted into the anonymised medical records database 18. It will be appreciated that the selection of records from the Journal table 40 and the Patients table 30 described above is provided by way of example, and that records can be selected from the Journal table 40 and the Patients table 30 in any convenient way.

From the subset of records selected from the Patients table 30, values stored in the PatientID field 31, Sex field 34a, DoB field 34b, Postcode field 34c, Deceased field 34d, DeathDate field 34e, Height field 34f, Weight field 34g, EthnicOrigin field 34h and UpdatedDate field 36 are read. Similarly, for the selected records of the Journal table 40 values stored in the PatientID field 41, EntryDate field 44, Rubric field 45, ReadCode field 46, CodeValue field 47, CodeUnits field 48, UpdatedTime field 49, Source field 50, DocumentGUID 51 and SectionGUID field 52 are read. The remaining fields of the selected records are disregarded.

From the selected data, it is possible that values of the PatientID field 31, Postcode field 34c, DoB field 34b and DeathDate field 34e could be used alone or in combination to identify a particular patient, and for each selected record, the values in these fields are transformed before the records are inserted into the anonymised medical records database 18, as is now described.

From step S1 processing passes to step S2, at which each unique PatientID value in the selected records is mapped to a respective unique randomly generated thirty-two-bit integer. It will be appreciated that, as the generated integer is random, there is nothing to link a particular generated integer with a particular patient's record. A list of all generated random integers is stored at the server 15, against which each newly generated random integer is checked to ensure that no two patients are assigned the same randomly generated integer.

Processing then passes to step S3 and for each record, the value read from the Postcode field 34*c* is mapped to a corresponding Lower Layer Super Output Area for that postcode (as published by the UK government Office for National Statistics (ONS)). Each Lower Layer Super Output Area (LLSOA) defines a geographical area generally large enough to preclude the identification of any particular individual. It will be appreciated that indicators of geographical location other than postcodes and LLSOA can be used, the requirement being that a second indicator identifies location less precisely than a first indicator.

Processing then passes to step S4 and, for each record, the date values in the DOB field 34*b* and DeathDate field 34*e* are mapped to a year value and a quartile value. For example, a date of first January nineteen-eighty-two would be mapped to a year value of nineteen-eighty-two and a quartile value of one. Similarly, a date of seventh July two-thousand-nine would be mapped to a year value of two-thousand-nine and a quartile value of three.

Processing then passes to step S5 at which data read from the selected records of the Patients table 30 and Journal table 40 is inserted into the anonymised medical records database 18. In more detail, for each record selected from the Patients table 30, a record in the Demographics table 60 is created. The random integer generated at step S2 is stored in the TransformedPatientID field 61, the mapped Lower Layer Super Output Area generated at step S3 is stored in the LLSOA field 62, the mapped date of birth year value is stored in the YearOfBirth field 63, the mapped date of birth quartile is stored in the QuartileOfBirth field 64, the mapped DeathDate year value is stored in a YearOfDeath field 65 and the mapped quartile of death is stored in a QuartileOfDeath field 66. The Sex, Deceased, UpdatedDate, Height, Weight and EthnicOrigin fields are populated directly from the corresponding fields of each record selected from the Patients table 30.

For each record selected from the Journal table 40, a record in the Clinical Events table 70 is created. The random integer generated at step S2 is stored in the TransformedPatientId field 71, and the EntryDate, Rubric, ReadCode, CodeValue, CodeUnits, Source, DocumentGUID, SectionGUID and UpdatedDateTime fields are populated directly from the corresponding fields of each record selected from the Journal table 40.

It will be appreciated that because anonymisation of records to be inserted into the anonymised medical records database 18 is performed before those records are inserted, no patient-identifiable data crosses the notional clinical care boundary 29. That is, only anonymised data is provided to the server 17 hosting the anonymised medical records database 18.

An overview of the system architecture and structure of the databases has been described above. The process of clinical trial feasibility assessment and recruitment according to an embodiment of the present invention is now described with reference to FIG. 2 and the flowchart of FIG. 6.

Figure 6:
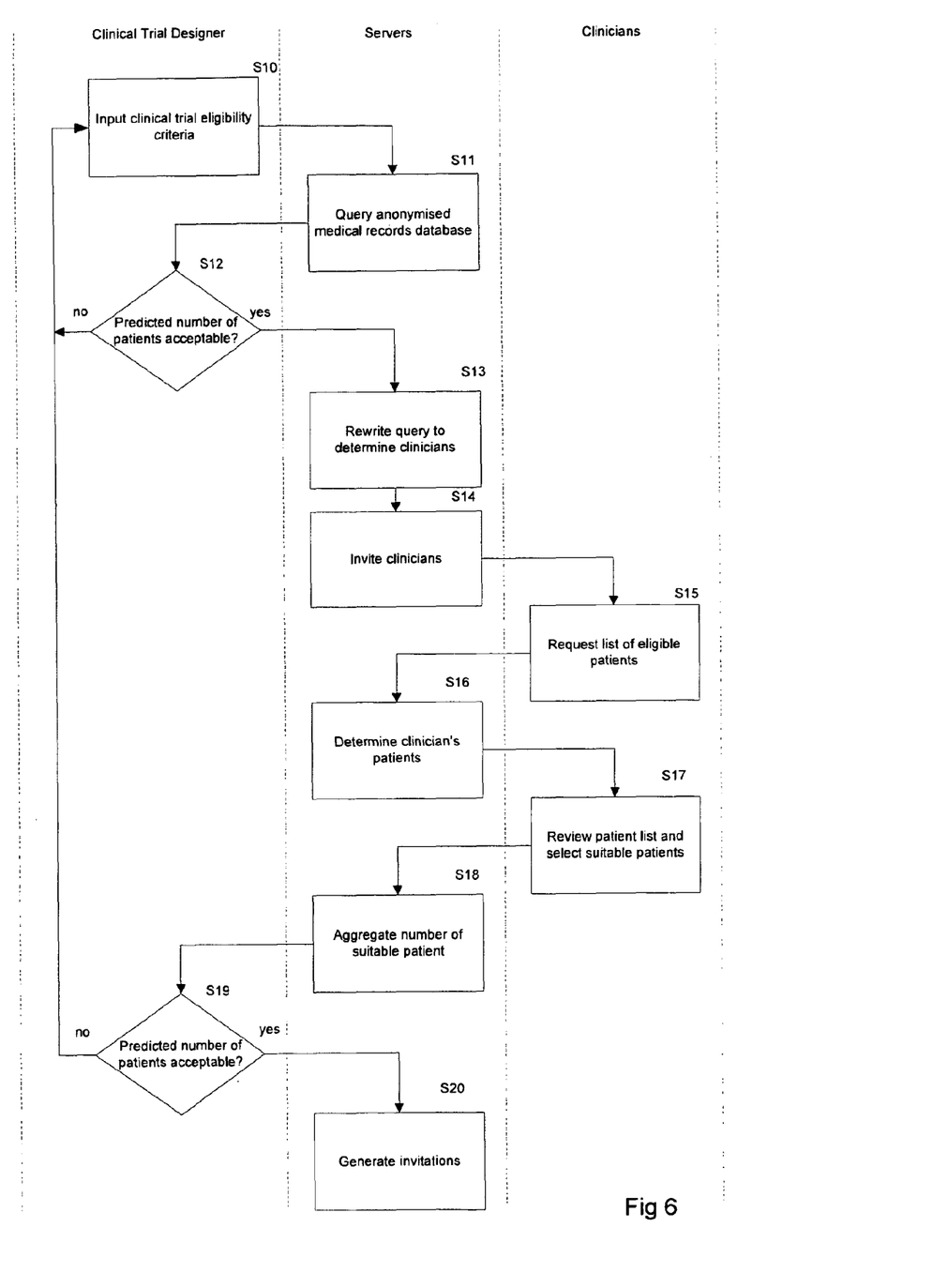
FIG. 6 is a flow chart showing processing carried out to determine feasibility of, and conduct recruitment for, a clinical trial in an embodiment of the present invention.

Referring to FIG. 6, at step S10 the clinical trial designer 22 accesses the trial protocol design application 20 to input eligibility criteria for a particular clinical trial for which the clinical trial designer wishes to recruit participants.

Figure 7:
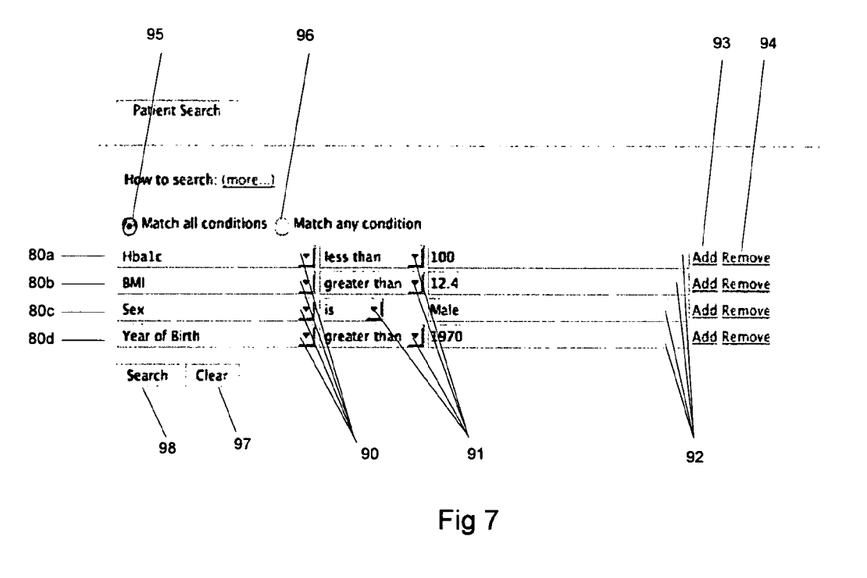
FIG. 7 shows an interface provided by the system of FIG. 2 to receive clinical trial eligibility criteria.

The trial protocol design application 20 is configured to receive clinical trial eligibility criteria from a clinical trial designer 22 and to determine a number of patients who are eligible to participate in the clinical trial by querying the anonymised medical record database 4. FIG. 7 is a screenshot of an interface provided by the trial protocol design application 20 that allows the clinical trial designer 22 to input trial eligibility criteria and submit those trial eligibility criteria for querying against the anonymised medical records database 18.

The interface shown in the screenshot of FIG. 7 allows the trial designer 22 to specify one or more conditions 80 which can be used to query the anonymised medical records database 18. Each respective condition is comprised of an attribute, selected from a respective drop-down menu 90, and a criterion that the selected attribute must match. The trial designer 22 specifies the criterion for each condition 80 using a respective drop down menu 91 and a respective text box 92. Each respective drop-down menu 91 allows the trial designer to specify a qualifier such as 'greater than', 'less than' or 'is' (equals), while the text box 92 allows the trial designer to specify the required attribute value. For example, a patient record will match a condition 80*a* in FIG. 7 if that patient record has an Hb1Ac measurement of less than 7.5%.

Add buttons 93 allow a trial designer 22 to add further conditions 80 to the eligibility criteria, while remove buttons 94 allow a user to remove a particular condition 80 from the eligibility criteria.

Selection of a radio button 95 indicates that eligibility for a clinical trial requires a patient to match all of the conditions 80, while selection of a radio button 96 indicates that eligibility for that clinical trial requires only that a patient match at least one of the conditions 80. A clear button 97 clears all of the conditions 80. A search button 98 transmits the eligibility requirements (comprised of the conditions 80 and the matching criteria as determined by selection of one of the radio buttons 95, 96) to the trial protocol design application 20. Having input the trial eligibility criteria and selected the search button 98, processing passes to step S11.

At step S11, the trial protocol design application 20 uses the eligibility criteria to generate an SQL query to run against the anonymised medical records database 18 and return a count of the number of patients who meet the submitted eligibility criteria.

Where a particular condition 80 has an attribute (specified using the dropdown menu 90) having a corresponding Read Code, a search is performed on the ClinicalEvents table 70 to find records that have a value matching that Read Code in the ReadCode field 74. For each matching record, it can then be determined if the value in the CodeValue field 75 meets the criteria of that condition 80 (specified using the respective dropdown menu 91 and the respective text box 92). If this is the case, the patient to whom that record relates satisfies that condition 80.

It may be that a plurality of Read Codes are in use to record data relating to a single attribute, and it may be that for any particular attribute, different, or non-standard, Read Codes are used to record information about that attribute in the Journal table 40 which are then copied to the ClinicalEvents table 70. The use of multiple Read Codes to record the same information could lead to the trial protocol design application 20 failing to identify all eligible patients if not all of the Read Codes used to record a particular attribute are included in a search for that attribute. To overcome this, a suggested list of Read Codes associated with particular attributes could be presented to the trial designer 22 in response to selection of a particular attribute in a drop down menu 90. The trial designer could then choose which Read Codes to include in the search, and in particular, whether to include non-standard Read Codes. For example, if the trial designer 22 wishes to search for patients with blood pressure between a certain range, a list of Read Codes which it is known are used to record blood pressure information can be presented to the trial designer 22. The trial designer 22 can then select which of the presented Read Codes he wishes to include in the search.

Where a condition 80 has an attribute that corresponds to a field in the Demographics table 60, a search is performed on the Demographics table 60 to find records having a value matching the criterion of that condition 80 in the corresponding field. For example, considering the condition 80c, a search would be performed on the Demographics table 60 to find records where the Sex field 82 has a value indicating 'Male'.

Having run the query at step S11 it is determined how many patients meet the eligibility criteria by determining how many unique transformed patient IDs are present in the records which match one of the conditions 80, and if the radio button 96 is selected, how many of those unique transformed patient IDs match every condition 80. The number of eligible patients is then returned to the trial designer 22 and processing passes to step S12.

At step S12, the trial designer 22 decides whether the number of eligible patients returned at step S11 is acceptable. If the trial designer decides that the number of patients is not acceptable, processing passes back to step S10 and the trial designer 22 interacts with the trial protocol design application 20 to test a new set of eligibility criteria by submitting a new set of conditions 80. The trial designer 22 can continue to alter the conditions 80 until a desired number of eligible patients is returned from the trial protocol design application 20. For example, if the trial designer 22 initially specifies that the age of a patient must be within a certain range and it is indicated that there are too few eligible patients within that age range, the trial designer could modify the conditions 80 to increase the specified age range.

To aid the trial designer 22 in altering the eligibility criteria, the trial protocol design application 20 may return more detailed information, rather than merely returning an integer number of patients matching the eligibility criteria. For example, for each one of the conditions 80, the trial protocol design application 20 may return a count of patients who satisfy that condition. From this, the trial designer is able to see the impact of each condition on the overall total number of eligible patients.

It will be appreciated that while the trial designer can only interrogate the anonymised medical records database 18, and is only provided with an integer number of patients, allowing the trial designer 22 to submit multiple queries creates the possibility of deductive disclosure of patients' personal details. For example, if the trial designer knows that his next-door neighbour is asthmatic, and if a query of the form "+asthma" restricted to the trial designer's Lower Level Super Output Area (LLSOA) returns a single result, then a subsequent query of the form "+asthma+alcoholic" restricted to the same LLSOA will disclose to the trial designer whether or not their next-door neighbour is an alcoholic. It may therefore be desirable for the trial protocol design application 20 to return a minimum number of patients in response to queries that would otherwise return a number of patients below that minimum number. For example, five may be an appropriate minimum number.

If, at step S12, the trial designer 22 decides that the number of patients returned at step S11 is acceptable, processing passes to step S13 at which the SQL query created by the trial protocol design application 20 based upon the input trial eligibility criteria is sent to the trial recruitment application 24 running on the server 15. Upon receiving the SQL query, the trial recruitment application 24 sends the SQL query to the query translation module 28.

The query translation module 28, rewrites the SQL query for execution against the medical records database 16 to return a set of the clinicians responsible for the patients meeting the conditions specified by the clinical trial designer 22. Processing then passes to step S14.

At step S14, the rewritten SQL query is executed on the medical records database 16 and the results are transmitted to trial recruitment application 24. The trial recruitment application 24 then sends a notification, via email, to each clinician 26 identified in the results of the rewritten SQL query, that they have patients eligible for a clinical trial.

From step S14, processing passes to step S15 at which each identified clinician 26 accesses the trial recruitment application 24 to obtain a list of their eligible patients. For example, a link may be provided within the notification email sent to each clinician, wherein selection of the link by a clinician 26 generates a request for a patient list which is sent to the trial recruitment application 24.

When a particular clinician 26 requests a list of their eligible patients at step S15, processing passes to step S16 and the trial recruitment application 24 re-issues the SQL query to the query translation module 28 together with the identity of the particular clinician 26 making a request for their eligible patients. The query translation module 28 then rewrites the query for execution against the medical records database 16 to return the identities of all eligible patients under the care of the requesting clinician 26. The rewritten query is executed on the medical records database 2 and the results are transmitted to the trial recruitment application 24 to be presented to the clinician 26.

Processing passes from step S16 to step S17 at which a clinician 26 reviews the list of their eligible patients to determine which of the listed patients should be sent invitations for recruitment into the trial. For example, the clinician 26 may be aware of a patient's personal circumstances that would preclude that patient from taking part in the clinical trial. Details of the trial eligibility criteria in the form of the conditions 80 may also be transmitted to the clinician 26 to allow the clinician 26 to better understand why particular patients under their care have been deemed eligible. It will be appreciated that steps S15, S16, S17 are repeated for each clinician 26 identified as having patients eligible for the clinical trial.

After each clinician 26 who has patients eligible for the trial has selected their eligible patients, processing passes to step S18 and the trial recruitment application 24 transmits the total number of selected patients to the trial protocol design application 20 for review by the trial designer 22.

At step S19 the trial designer 22 determines whether the total number of patients, selected by the clinicians 26 responsible for those patients, is acceptable. If the trial designer 22 decides that the total number of patients is unacceptable, processing passes back to step S10 so that the trial designer can alter the eligibility criteria for the trial.

If, on the other hand, at step S19, the trial designer determines that the total number of patients is acceptable, the trial designer 22 indicates to the trial protocol design application 20 that trial recruitment can begin. Processing then passes to step S20 at which the trial recruitment application 24 automatically generates personalised invitation letters (or other correspondence, for example, email) for the each clinician 26 to send to their patients. If a patient agrees to take part in the clinical trial, that patient's details may be provided to the trial designer 22, or a different user responsible for conducting the clinical trial.

It is described above how embodiments of the present invention can be used to perform feasibility analysis for use in the design of clinical trials, and for recruitment of patients into the clinical trial while maintaining the requirements of privacy.

It will be appreciated that the present invention has applications extending beyond the use in the design of and recruitment for clinical trials as described above. Indeed, the present invention has application in any area where it is required to maintain privacy of data across a notional boundary. For example, the present application may be used in banking applications where it is it is desirable to provide one set of users, possibly external to the bank, with limited access to customers' financial data.

Further modifications and applications of the present invention will be readily apparent to the appropriately skilled person from the teaching herein, without departing from the scope of the appended claims.

The invention claimed is:

1. A method for allowing an at least one unauthorized user to access select data contained in an at least one secure database while maintaining the privacy of an at least one subject to which the data relates, the method comprising the steps of:
   hosting the at least one secure database on an at least one server, the at least one secure database containing a plurality of secure records within which the data is stored, each of said secure records containing data associated with at least one subject;
   hosting an at least one anonymized database on the at least one server, the at least one anonymized database containing a plurality of anonymized records, each of the anonymized records containing an at least one anonymized version of select data associated with a corresponding one of the secure records in the at least one secure database such that the associated at least one subject cannot be identified; and
   upon a one of the at least one unauthorized user selectively accessing the at least one anonymized database:
   receiving an at least one specified criterion from said unauthorized user;
   performing a search of the anonymized database to determine whether any of the anonymized records contain data meeting the at least one specified criterion; and
   upon identifying at least one of the anonymized records that contains data meeting the at least one specified criterion:
   performing a search of the secure database, based on the at least one specified criterion, to access each of the at least one respective secure record corresponding to the at least one identified anonymized record;
   determining an at least one authorized user for each of the at least one identified anonymized records, each said authorized user being authorized to access the secure record corresponding to the at least one identified anonymized record;
   receiving confirmation from the at least one authorized user regarding whether said at least one subject meets the at least one specified criterion; and for each of the at least one identified anonymous record for which confirmation has been received from the at least one authorized user:
   transmitting a notification to the at least one subject associated with said identified anonymous record; and
   upon receiving approval from the at least one subject associated with said identified anonymous record, providing said unauthorized user with necessary data contained in the associated secure record.

2. The method of claim 1, further comprising the step of hosting each of the at least one secure database and anonymized database on separate servers, the at least one secure database being stored on an at least one server to which the at least one unauthorized user does not have access.

3. The method of claim 1, wherein the step receiving confirmation from the at least one authorized user further comprises the step of
   transmitting a notification to each of the at least one authorized user regarding the at least one subject associated with said identified anonymized records.

4. The method of claim 3, wherein the step of transmitting a notification to each of the at least one authorized user regarding the at least one subject associated with said identified anonymized records further comprises the step of providing the at least one authorized user with the at least one specified criterion.

5. The method of claim 3, further comprising the step of, upon identifying at least one of the anonymized records that contains data meeting the at least one specified criterion, providing said unauthorized user with an initial count of a number of subjects based upon said identified anonymized records.

6. The method of claim 5, further comprising the steps of, upon said unauthorized user indicating that the initial count is unacceptable:
   receiving an at least one revised specified criterion from said unauthorized user;
   performing a search of the anonymized database to determine whether any of the anonymized records contain data meeting the at least one revised specified criterion; and
   upon identifying at least one of the anonymized records that contains data meeting the at least one revised specified criterion, providing said unauthorized user with a revised initial count of a number of subjects based upon said identified anonymized records.

7. The method of claim 5, further comprising the step of, upon identifying at least one of the anonymized records that contains data meeting the at least one specified criterion, providing said unauthorized user with a confirmed count of a number of subjects based on the confirmation received from the at least one authorized user.

8. The method of claim 7, further comprising the steps of, upon said unauthorized user indicating that the confirmed count is unacceptable:
   receiving an at least one revised specified criterion from said unauthorized user;
   performing a search of the anonymized database to determine whether any of the anonymized records contain data meeting the at least one revised specified criterion; and
   upon identifying at least one of the anonymized records that contains data meeting the at least one revised specified criterion, providing said unauthorized user with a revised confirmed count of a number of subjects based on the confirmation received from the at least one authorized user.

9. The method of claim 1, further comprising the step of populating the at least one anonymized database.

10. The method of claim 9, wherein the step of populating the at least one anonymized database further comprises the steps of:
obtaining select data from at least one of the secure records in the at least one secure database;
anonymizing said select data; and
inserting the anonymized data into corresponding anonymized records associated with the at least one secure record from which the select data was obtained.

11. The method of claim 10, wherein the step of anonymizing select data from at least one of the secure records further comprises the steps of, for each of the at least one associated secure record:
generating a unique randomly generated anonymized identifier; and
mapping the anonymized identifier to a unique record identifier associated with said secure record.

12. The method of claim 11, further comprising the steps of, for each of the at least one associated secure record:
upon determining that a given data value associated with said secure record indicates a geographic location associated with the at least one subject, converting said geographic location to a relatively less precise anonymized geographic area; and
upon determining that a given data value associated with said secure record indicates a date containing at least a month, converting said month to a relatively less precise quartile.

13. The method of claim 1, wherein the step of performing a search of the anonymized database to determine whether any of the anonymized records contain data meeting the at least one specified criterion further comprises the step of searching the anonymized database using a first database query containing the at least one specified criterion.

14. The method of claim 13, wherein the step of accessing each of the at least one respective secure record corresponding to the at least one identified anonymized record further comprises the steps of:
processing the first database query to generate a second database query; and
searching the secure database using the second database query.

15. The method of claim 1, wherein the step of transmitting a notification to each of the at least one authorized user regarding the at least one subject associated with said identified anonymized records further comprises the step of providing the at least one authorized user with only the secure records with which said authorized user is associated.

16. A method for allowing an at least one unauthorized user to access select data contained in an at least one secure database while maintaining the privacy of an at least one subject to which the data relates, the method comprising the steps of:
hosting the at least one secure database on an at least one server, the at least one secure database containing a plurality of secure records within which the data is stored, each of said secure records containing data associated with at least one subject;
hosting an at least one anonymized database on the at least one server, the at least one anonymized database containing a plurality of anonymized records, each of the anonymized records containing an at least one anonymized version of select data associated with a corresponding one of the secure records in the at least one secure database such that the associated at least one subject cannot be identified; and
upon a one of the at least one unauthorized user to selectively accessing the at least one anonymized database:
receiving an at least one specified criterion from said unauthorized user;
performing a search of the anonymized database to determine whether any of the anonymized records contain data meeting the at least one specified criterion; and
upon identifying at least one of the anonymized records that contains data meeting the at least one specified criterion:
performing a search of the secure database, based on the at least one specified criterion, to access each of the at least one respective secure record corresponding to the at least one identified anonymized record;
determining an at least one authorized user for each of the at least one identified anonymized records, each said authorized user being authorized to access the secure record corresponding to the at least one identified anonymized record;
transmitting a notification to each of the at least one authorized user regarding the at least one subject associated with said identified anonymized records;
receiving confirmation from the at least one authorized user regarding whether said at least one subject meets the at least one specified criterion; and
for each of the at least one identified anonymous record for which confirmation has been received from the at least one authorized user:
transmitting a notification to the at least one subject associated with said identified anonymous record; and
upon receiving approval from the at least one subject associated with said identified anonymous record, providing the unauthorized user with necessary data contained in the associated secure record.

17. A system configured for allowing an at least one unauthorized user to access select data contained in an at least one secure database while maintaining the privacy of an at least one subject to which the data relates, the system comprising at least one processor coupled to a memory:
an at least one secure database residing on an at least one server, the at least one secure database containing a plurality of secure records within which the data is stored, each of said secure records containing data associated with at least one subject;
an at least one anonymized database residing on the at least one server, the at least one anonymized database containing a plurality of anonymized records, each of the anonymized records containing an at least one anonymized version of select data associated with a corresponding one of the secure records in the at least one secure database such that the associated at least one subject cannot be identified; and
wherein, upon a one of the at least one unauthorized user selectively accessing the at least one anonymized database;
the at least one processor executes the steps of:
receiving an at least one specified criterion from said unauthorized user;
performing a search of the anonymized database to determine whether any of the anonymized records contain data meeting the at least one specified criterion; and upon identifying at least one of the anonymized records that contains data meeting the at least one specified criterion:

performing a search of the secure database, based on the at least one specified criterion, to access each of the at least one respective secure record corresponding to the at least one identified anonymized record;

determining an at least one authorized user for each of the at least one identified anonymized records, each said authorized user being authorized to access the secure record corresponding to the at least one identified anonymized record;

receiving confirmation from the at least one authorized user regarding whether said at least one subject meets the at least one specified criterion; and for each of the at least one identified anonymous record for which confirmation has been received from the at least one authorized user:

transmitting a notification to the at least one subject associated with said identified anonymous record; and upon receiving approval from the at least one subject associated with said identified anonymous record, providing said unauthorized user with necessary data contained in the associated secure record.

18. The system of claim 17, wherein the at least one unauthorized user is a researcher.

19. The system of claim 18, wherein the at least one authorized user is a clinician.

20. The system of claim 19, wherein the at least one subject is a patient of the associated clinician.

* * * * *